(12) United States Patent
Bristow

(10) Patent No.: US 9,668,483 B1
(45) Date of Patent: Jun. 6, 2017

(54) SYNERGISTIC HERBICIDAL COMPOSITION AND USE THEREOF

(71) Applicant: ROTAM AGROCHEM INTERNATIONAL COMPANY LIMITED, Chai Wan, Hong Kong (CN)

(72) Inventor: James Timothy Bristow, Hong Kong (CN)

(73) Assignee: ROTAM AGROCHEM INERNATIONAL COMPANY LIMITED, Chai Wan (HK)

(*) Notice: Subject to any disclaimer, the term of this patent is extended or adjusted under 35 U.S.C. 154(b) by 0 days.

(21) Appl. No.: 14/955,220

(22) Filed: Dec. 1, 2015

(51) Int. Cl.
*A01N 41/10* (2006.01)
*A01N 47/36* (2006.01)
*A01N 25/12* (2006.01)
*A01N 25/14* (2006.01)

(52) U.S. Cl.
CPC ............ *A01N 47/36* (2013.01); *A01N 41/10* (2013.01)

(58) Field of Classification Search
CPC combination set(s) only.
See application file for complete search history.

(56) References Cited

U.S. PATENT DOCUMENTS

| 4,954,628 A | 9/1990 | Besenyei et al. | |
| 5,550,238 A * | 8/1996 | Chiang | C07D 521/00 544/206 |
| 2010/0166023 A1* | 7/2010 | Fisher | H04N 7/54 370/503 |
| 2015/0031877 A1* | 1/2015 | Hiratsuka | A01N 43/84 544/105 |

FOREIGN PATENT DOCUMENTS

| CN | 102391194 A | 3/2012 |
| CN | 102487946 | * 6/2012 |
| CN | 102718723 A | 10/2012 |
| EP | 202830 | * 11/1986 |
| EP | 0202830 A1 | 11/1986 |
| WO | WO 2006/021743 | * 3/2006 |

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*
Roberts, R.M. et al. Modern Experimental Organic Chemistry. Holt, Rinehart and Winston, New York, 1979, pp. 49-58.*
HCAPLUS abstract 1999:261209 (1999).*
HCAPLUS abstract 2012-856200; abstracting CN 102487946 (2012).*
Machine translation of CN 102487946 (2012).*
Herbicide Handbook, Weed Science Society of America, Seventh Edition—1994, p. 318.
International Search Report for PCT/CN2016/098395 dated Dec. 12, 2016.
Office Action for 14/955,147 dated Sep. 21, 2016.
Cui, Yu-jie et al.; Study on the Synthesis of Tribenuron-methyl from Triphosgene, Fine Chemical Intermediates, vol. 43 No. 2 Apr. 2013.
Li, Hui-qin et al.; Study on the Herbicide Tribenuron-methyl, Fine and Speciality Chemicals, vol. 15, No. 13.
Lu, Yang et al.; Synthesis of Tribenuron-methyl; Worth Pesticides, vol. 29, No. 2 Apr. 2007.
Zhao, Bangbin et al., Synthesis of Herbicides Sulfonylurea by Bis (trichloromethyl) Carbonate, vol. 42 No. 7 (2003).

* cited by examiner

*Primary Examiner* — John Pak
(74) *Attorney, Agent, or Firm* — Dickinson Wright PLLC

(57) ABSTRACT

A herbicidal composition is provided, the composition comprising: (A) the crystalline modification I of 2-(4-mesyl-2-nitrobenzoyl)cyclohexane-1,3-dione (mesotrione); and (B) the crystalline modification I of methyl 2-[[[[(4-methoxy-6-methyl-1,3,5-triazin-2-yl)methylamino]carbonyl]amino] sulfonyl]benzoate (tribenuron-methyl). A method of controlling plant growth at a locus comprises applying to the locus herbicidally effective amounts of both (A) the crystalline modification I of 2-(4-mesyl-2-nitrobenzoyl)cyclohexane-1, 3-dione (mesotrione); and (B) the crystalline modification I of 2-[[[[(4-methoxy-6-methyl-1,3,5-triazin-2-yl)methyl-amino]carbonyl]amino]sulfonyl]benzoate (tribenuron-methyl).

32 Claims, 4 Drawing Sheets

SYNERGISTIC HERBICIDAL COMPOSITION AND USE THEREOF

BACKGROUND

1. Field

The present disclosure relates to a synergistic herbicidal composition containing mesotrione and tribenuron-methyl, each in particular crystal modifications. The composition finds use in controlling the growth of undesirable plant, particularly in crops, including using the aforementioned composition.

2. Description of Related Art

The protection of crops from undesirable plant, which inhibits crop growth, is a constantly recurring problem in agriculture. To solve this problem, researchers are trying to produce an extensive variety of chemicals and chemical formulations effective in the control of such undesirable growth. Chemical herbicides of many types have been disclosed in the literature and a large number are in commercial use.

Some herbicidal active ingredients have been shown to be more effective when applied in combination rather than applied individually, this effect being referred to as "synergism." According to *Herbicide Handbook* of the Weed Science Society of America, Seventh Edition, 1994, page 318, "synergism" is an interaction of two or more factors such that the effect when combined is greater than the predicted effect based on the response to each factor applied separately.

The compound 2-(4-mesyl-2-nitrobenzoyl)cyclohexane-1,3-dione has the common name "mesotrione." Mesotrione is a substance that can form polymorph crystals. Two different forms, crystalline modifications I and II, of mesotrione are described in WO2006021743, which is incorporated herein by reference for all purposes. Mesotrione is active as a herbicide, and is now commercially available in a range of formulations for controlling the growth of undesirable plant. Crystalline modification I of mesotrione is reported to have the following XRD spectrum, although some peak shifting may be possible:

| Peak Position (2-Theta) | Peak Position (d spacing) |
| --- | --- |
| 8.52 | 10.34 |
| 17.08 | 5.18 |
| 17.43 | 5.08 |
| 18.74 | 4.73 |
| 19.04 | 4.66 |
| 19.31 | 4.59 |
| 19.52 | 4.54 |
| 21.15 | 4.20 |
| 25.73 | 3.46 |
| 28.66 | 3.11 |

The compound methyl 2-[[[[(4-methoxy-6-methyl-1,3,5-triazin-2-yl)methylamino]carbonyl]amino]sulfonyl]benzoate, having the common name "tribenuron-methyl," is a known herbicide. Tribenuron-methyl is a selective post-emergence sulfonylurea herbicide for the control of broad-leaved weeds in cereals and sunflower. It can be manufactured by the process described in EP 0202830, which is incorporated herein by reference, where it is present in an amorphous state which is highly viscous.

SUMMARY

Due to its viscosity, the amorphous state of tribenuron-methyl has a poor spray equipment clean-out property and will heavily contaminate the spray equipment. It has been found that a crystal form of tribenuron-methyl, "crystalline modification I", has an improved spray equipment clean-out property and reduces residual tribenuron-methyl contamination of spray equipment (U.S. Ser. No. 14/955,147, filed on even date herewith, and incorporated herein by reference for all purposes). The crystalline modification I of tribenuron-methyl exhibits at least 3 of the following reflexes, in any combination, as 2θ values in an X-ray powder diffractogram recorded using Cu—Kα radiation at 25° C.:

| | |
| --- | --- |
| $2\theta = 6.47 \pm 0.2$ | (1) |
| $2\theta = 10.46 \pm 0.2$ | (2) |
| $2\theta = 11.02 \pm 0.2$ | (3) |
| $2\theta = 14.01 \pm 0.2$ | (4) |
| $2\theta = 15.73 \pm 0.2$ | (5) |
| $2\theta = 16.71 \pm 0.2$ | (6) |
| $2\theta = 16.98 \pm 0.2$ | (7) |
| $2\theta = 21.04 \pm 0.2$ | (8) |
| $2\theta = 22.23 \pm 0.2$ | (9) |
| $2\theta = 23.26 \pm 0.2$ | (10) |
| $2\theta = 25.01 \pm 0.2$ | (11) |
| $2\theta = 26.14 \pm 0.2$ | (12) |

Crystalline modification I mesotrione produced by the process disclosed herein may have a somewhat shifted XRD spectrum, such as:

| Peak Position (2-Theta) | Peak Position (d spacing) |
| --- | --- |
| 8.44 | 10.47 |
| 17.35 | 5.11 |
| 17.55 | 5.05 |
| 18.67 | 4.75 |
| 18.98 | 4.68 |
| 19.24 | 4.61 |
| 19.45 | 4.56 |
| 21.06 | 4.22 |
| 25.64 | 3.47 |
| 28.55 | 3.13 |

It has been surprisingly found that combining the crystalline modification I of mesotrione with the crystalline modification I of tribenuron-methyl provides a composition having a synergistic activity, that is, an increased herbicidal activity, compared with the activity expected from the activity of the two components when applied individually.

Accordingly, in a first aspect, the invention provides a herbicidal composition comprising:

(A) the crystalline modification I of 2-(4-mesyl-2-nitrobenzoyl)cyclohexane-1,3-dione (mesotrione); and (B) the crystalline modification I of methyl 2-[[[[(4-methoxy-6-methyl-1,3,5-triazin-2-yl)methylamino]carbonyl]amino]sulfonyl]benzoate (tribenuron-methyl).

The composition of an embodiment of the invention is of particular use for controlling the growth of undesirable plant.

In a second aspect, the invention provides a method of controlling the growth of undesirable plant comprising applying to the plant or to the locus thereof a herbicidally effective amount of the herbicidal composition of the first aspect of the invention.

In a further aspect, the invention provides the use of the herbicidal composition of the first aspect of the present invention in control of undesirable plant growth at a locus.

DETAILED DESCRIPTION OF SPECIFIC EMBODIMENTS

Figure 1:
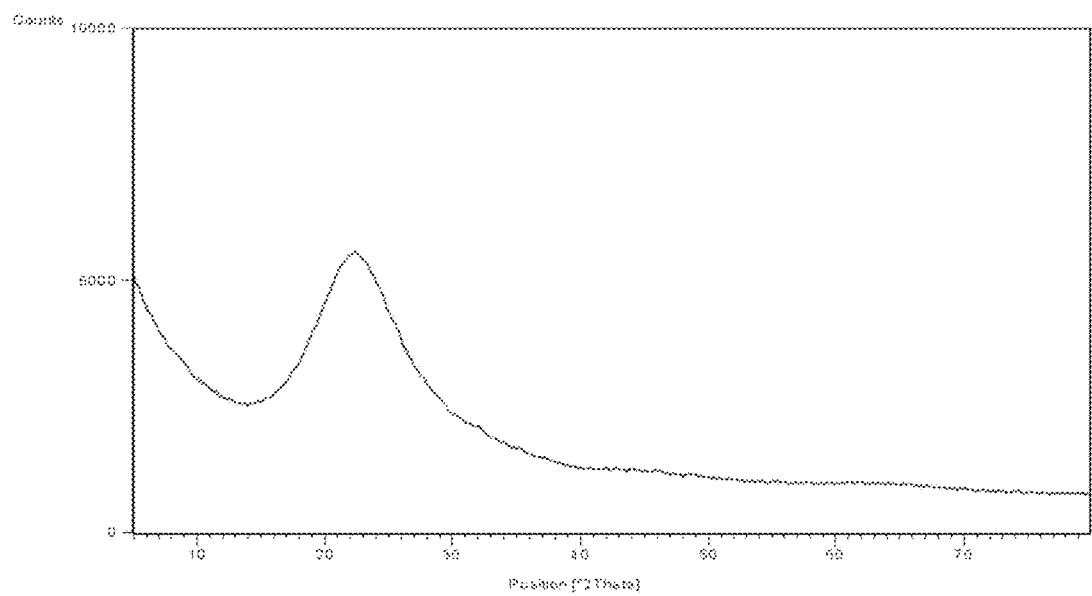
FIG. 1 is a graph showing the results of a X-ray powder diffractogram of amorphous tribenuron-methyl.

The references to the crystalline modifications I and II of mesotrione as used herein, refer to the crystalline modification of mesotrione disclosed in WO2006021743, where they are described as Form I and Form II, respectively.

The term "herbicide" as used herein, refers to a compound that controls the growth of plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

The term "plants" refers to all physical parts of a plant, including shoots, leaves, needles, stalks, stems, fruit bodies, fruits, seeds, roots, tubers and rhizomes.

The term "locus" refers to the place on which the plants are growing, the place on which the plant propagation materials of the plants are sown or the place on which the plant propagation materials of the plants will be sown.

"At least one" designates a number of the respective compounds or components of 1, 2, 3, 4, 5, 6, 7, 8, 9 or more, preferably 1, 2, or 3.

The synergistic herbicidal composition, the method and use of the present invention are suitable for controlling undesirable plant in a range of crops, including: cereals, for example wheat, barley, rye, oats, corn, rice, sorghum, triticale and related crops; fruit, such as pome fruit, stone fruit and soft fruit, such as apples, pears, plums, peaches, pistachio, almonds, cherries, and berries, for example grape, banana, strawberries, bushberry, caneberry, raspberries and blackberries; leguminous plants, for example beans, lentils, peas, and soybeans; oil plants, for example oilseed rape, mustard and sunflowers; cucurbitaceae, for example cantaloupe, marrows, cucumbers, melons, pumpkin, squash and watermelon; citrus fruit, such as oranges, lemons, grapefruit and mandarins; and vegetables, for example spinach, lettuce, asparagus, cabbages, carrots, onions, tomatoes, potatoes, paprika, garlic and leeks; coffee; sugarcane; hops; tree nuts; as well as ornamentals, for example flowers, such as roses, shrubs, broad-leaved trees and evergreens, such as conifers. Preferably, the composition described herein is used to treat cereals, sugarcane, vegetables and oil plants. More preferably, the composition described herein is used to treat wheat, barley, rye, oats, corn, triticale, sugarcane, vegetables and oilseed rape.

The control of undesirable plant in such crops may be achieved by applying to the locus (A) the crystalline modification I of 2-(4-mesyl-2-nitrobenzoyl)cyclohexane-1,3-dione (mesotrione), which is identified as Form I in WO 2006/021743 and (B) the crystalline modification I of methyl 2-[[[[(4-methoxy-6-methyl-1,3,5-triazin-2-yl)methylamino]carbonyl]amino]sulfonyl]benzoate (tribenuron-methyl) in suitable amounts.

The active compounds (A) and (B) may be applied to the locus together or separately. If applied separately, active compounds (A) and (B) may be applied at the same time and/or consecutively. The control may comprise applying to the plant or the locus thereof a herbicidally effective amount of the herbicidal composition.

It has been surprisingly found that a combination of (A) the crystalline modification I of 2-(4-mesyl-2-nitrobenzoyl) cyclohexane-1,3-dione (mesotrione) and (B) the crystalline modification I of methyl 2-[[[[(4-methoxy-6-methyl-1,3,5-triazin-2-yl)methylamino]carbonyl]amino]sulfonyl]benzoate (tribenuron-methyl) exhibits a synergistic action in the control of many weeds, particularly, but not limit to, broad-leaved weeds and grasses. For example, weeds treatable according to an embodiment of the invention include:

African Rue (*Peganum Harmala*), Alkali Mallow (*Malvella leprosa*), Alligatorweed (*Alternantha philoxeroides*), Alsike Clover (*Trifolium hybridum*), Amaranth (*Amaranthus* spp), Annual Broomweed (*Gutierrezia dracunculoides*), annual knawel, annual mercury (*Mercurialis annua*), Annual Pricklepoppy (*Argemone polyanthemos*), Annual Sowthistle (*Sonchus oleraceus*), Antelope Horn (*Asclepias viridis*), Asiatic Hawksbeard (*Youngia japonica*), Balsam Gourd (*Ibervillea lindheimeri*), Balsam-Apple (*Momordica charantia*), Bastard Toadflax (*Comandra umbellata*), Beggarweed (*Desmodium* spp.), Bindweed, Field (noxious) (*Convolvulus arvensis*), Bindweed, Hedge (*Convolvulus sepium*), Bindweed, Texas (*Convolvulus equitans*), Birdsfoot Trefoil (*Lotus corniculatus*), Bittercress, Small-flowered (*Cardamine parviflora*), Bitterweed (*Hymenoxys odorata*), Bitterweed, Brown (*Helenium badium*), Black Medic (*Medicago lupulina*), black mustard, Black Nightshade (*Solanum americanum*), Blackfoot Daisy (*Melampodium leucanthum*), Blackseed Plantain (*Plantago rugelii*), Bladderpod (*Lesquerella gracilis*), blue/purple mustard, Bracted Plantain (*Plantago aristata*), broadleaf dock, Broadleaf Plantains (*Plantago* spp.), Buckhorn Plantain (*Plantago lanceolata*), Buffalo Gourd (*Cucurbita foetidissima*), Buffalobur (*Solanum rostratum*), Bulbous Buttercup (*Ranunculus bulbosus*), Bull Thistle (*Cirsium vulgare*), bur buttercup, Bur Clover (*Medicago hispida*), Burcucumber (*Sicyos angulatus*), Bushy Buttonweed (*Spermacoce assurgens*), Bushy Wallflower (*Erysimum repandum*), bushy wallflower, Butterweed (*Senecio glabellus*), Camphorweed (*Heterotheca subaxillaris*), Canada Thistle (*Cirsium arvense*), Carolina False Dandelion (*Pyrrhopappus carolinianus*), Carolina geranium, Carpetweed (*Mollugo verticillata*), Catchweed Bedstraw (*Galium aparine*), Centella, Chamberbitter (*Phyllanthus urinaria*), Chicory (*Cichorium intybus*), Cinquefoil, Clammy Groundcherry (*Physalis heterophylla*), clasping pepperwee, Climbing Hempweed (*Mikania scandens*), coast fiddleneck, Coat Buttons (*Tridax procumbens*), Common Beggar-tick (*Bidens alba*), common buckwheat, Common Burdock (*Arctium* minus), Common Chickweed (*Stellaria media*), Common Cocklebur (*Xanthium strumarium*), Common Groundsel (*Senecio vulgaris*), Common Lambsquarters (*Chenopodium album*), Common Mallow, Common Milkweed (*Asclepias syriaca*), Common Mullein (*Verbascum thapsus*), common orache (*Atriplex patula*), Common Pokeweed (*Phytolacca americana*), Common Purslane (*Portulaca oleracea*), common radish, Common Ragweed (*Ambrosia artemiisifolia*), Common Sneezeweed (*Helenium amarum*), Common Sunflower (*Helianthus annuus*), Common Waterhemp (*Amaranthus rudis*), Common Yarrow (*Achillea millefolium*), Compass Plant (*Silphium laciniatum*), conical catchfly, Coreopsis (*Coreopsis tinctoria*), corn chamomile, Corn Gromwell (*Lithospermum arvense*), Corn Speedwell (*Veronica arvensis*), corn spurry, Cowcockle (*Vaccaria pyramidata*), Cowpen Daisy (*Verbesina encelioides*), Creeping Beggarweed (*Desmodium incanum*), creeping buttercup (*Ranunculus repens*), Creeping Cucumber (*Melothria pendula*), Creeping Indigo (*Indigofera spicata*), Creeping Oxalis, Creeping Speedwell, Creeping Woodsorrel (*Oxalis corniculata*), cress, Croton, Texas (*Croton texensis*), Croton, Tropic (*Croton glandulosus*), Croton, Woolly (*Croton capitatus*), Cup Plant (*Silphium perfoliatum*), Cupid's Shaving Brush (*Emilia sonchifolia*), Curly Dock (*Rumex crispus*), Curlycup Gumweed (*Grindelia squarrosa*), Cutleaf Eveningprimose (*Oenothera laciniata*), Cutleaf Groundcherry (*Physalis angulata*), Daisy Fleabane (*Erigeron annuus*), Dakota Verbena (*Verbena bipinnatifida*), Dandelion (*Taraxacum officinale*), Dayflower (*Commelina*), Deadnettle, Purple (*Lamium purpureum*), Devil's Claw (*Proboscidea louisianica*), Dichondra, Dogfennel (*Euphorbia capillifolium*), Elderberry (*Sambucus canadensis*), Englemann Daisy (*Englemannia pinnatifida*), false chamomile, False Daisy or Eclipta (*Eclipta prostrata*), False Nightshade (*Chamaesaracha coronopus*), field chickweed, Field Dodder (*Cuscuta campestris*), field pennycress, Filaree, California or Redstem (*Erodium cicutarium*), Filaree, Texas or Storkbill (*Erodium texanum*), fixweed, Flixweed (*Descurainia sophia*), Florida Pellitory (*Parietaria floridana*), Garden Rocket (*Eruca vesicaria* ssp. *sativa*), Garden Spurge (*Chamaesyce hirta*), Germander (*Teucrium cubense*), Giant Ragweed (*Ambrosia trifida*), Goldenrod (*Solidago* spp.), goosefoots (*Chenopodium* spp.), Gray Tidestrom (*Tidestromia lanuginosa*), great ragweed (*Ambrosia trifida*), Greenbriar (*Smilax* spp.), Greenthread (*Thelesperma filifolium*), Ground Spurge (*Euphorbia prostrata*), groundsel, Hairy Caltrop (*Kallstroemia hirsutissina*), Hairy Nightshade (*Solanum sarrachoides*), Hedge Parsley (*Torilis arvensis*), Hemp Dogbane (*Apocynum cannabinum*), Hemp Sesbania (*Sesbania exaltata*), Henbit (*Lamium amplexicaule*), Hogpotato (*Hoffmanseggia densiflora*), Honeysuckle (*Lonicera* spp.), Hophornbeam Copperleaf (*Acalypha ostryaefolia*), Horehound (*Marrubium vulgare*), Horse purslane (*Trianthema portulacastrum*), Horsenettle (*Solanum carolinense*), Horseweed (*Conyza canadensis*), Huisachedaisy (*Amblyolepis setigera*), Hyssop Spurge (*Chamaesyce hyssopifolia*), Illinois Bundleflower (*Desmanthus illinoensis*), Indian Blanket (*Gaillardia pulchella*), Indian Mallow (*Abutilon incana*), Japanese Hops (*Humulus japonicus*), Jerusalem Artichoke (*Helianthus tuberosus*), Jimsonweed (*Datura stramonium*), Khakiweed (*Alternanthera pungens*), knotweed (*polygonum* spp.), Kochia (*Kochia scoparia*), Kudzu (noxious) (*Pueraria lobata*), Lamb's-quarters (*Chenopodium album*), Lanceleaf Sage (*Salvania reflexa*), Lantana (*Lantana camara*), Livid Amaranth (*Amaranthus blitum*), Lizardtail Gaura (*Gaura Parviflora*), London rocket, Long Fruited Primrose-Willow (*Ludwigia octovalvis*), Marijuana (noxious) (*Cannabis sativa*), Marsh Parsley (*Cyclospermum leptophylum*), marshelder, Match-Head (*Phyla nodiflora*), mayweed chamomile, Mexicanhat (*Ratibida columnaris*), Mexican-Poppy (*Argemone mexicana*), miners lettuce, Mock Bishop's Weed (*Ptilimnium capillaceum*), Morningglory, Bigroot (*Ipomoea pandurata*), Morningglory, Ivyleaf (*Ipomoea hederacea*), Morningglory, Pitted (*Ipomoea lacunosa*), Morningglory, Sharppod (*Ipomoea trichocarpa*), Morningglory, Tall (*Ipomoea purpurea*), Mouseear Chickweed (*Cerastium vulgatum*), Mousetail (*Myosurus minimus*), Multiflora rose (noxious) (*Rosa multiflora*), Mustard, London Rocket (*Sisymbrium irio*), Mustard, Pinnatetansy (*Descurainia pinnate*), Mustard, Tansy (*Descurainia pinnata*), Mustard, Tumble (*Sisymbrium altissimum*), Mustard, Turnip Weed (*Rapistrum rugosum*), Mustard, Wild (*Brassica kaber*), narrowleaf lambsquarters, ightflowering catchfly, Nodding Spurge (*Euphorbia nutans*), Orange Globe Mallow (*Sphaeralcea occidentalis*), Oxeye Daisy (*Chrysanthemum leucanthemum*), Palmer Amaranth (*Amaranthus palmeri*), Partridgepea (*Cassia chamaecrista*), Pennsylvania smartweed, Pennycress, Field (*Thlaspi arvense*), pigweed, Pigweed, Prostrate (*Amaranthus blitoides*), Pigweed, Redroot (*Amaranthus retroflexus*), Pigweed, Tumble (*Amaranthus albus*), pineappleweed, plains coreopsis, Poison Hemlock (*Conium maculatum*), prickly lettuce, Prickly Pear (*Opuntia* spp.), Prickly *Sida* (*Sida spinosa*), Prostrate Knotweed (*Polygonum aviculare*), Puncturevine (*Tribulus terrestris*), Purple Flower Groundcherry (*Physalis lobata*), Purple Horsemint (*Monarda citriodora*), Purple Loosestrife (noxious) (*Lythrum salicaria*), Purslane Speedwell (*Veronica peregrina*), Rain Lily (*Cooperia drummondii*), Rattlesnake master (*Eryngium yuccifolium*), Red Hornedpoppy (*Glaucium corniculatum*), redmaids, redroot pigweed (*Amaranthus retroflexus*), Riddell Groundsel (*Senecio riddellii*), Rosinweed (*Silphium integrifolium*), rough cocklebur (*Xanthium strumarium*), Russian thistle, Saltmarsh Fleabane (*Pluchea odorata*), Santa Maria or Parthenium Pancake Weed (*Parthenium hysterophorus*), Sawtooth aster (*Prionopsis ciliata*), Scarlet Gaura (*Gaura coccinea*), Scarlet Musk Flower (*Nyctaginia capitata*), scentless chamomile, Scrambledeggs (*Corydalis curvisiliqua*), Shepherd's Purse (*Capsella bursa-pastoris*), Sicklepod (*Senna obtusifolia*), SilverLeaf *Cassia* (*Cassia phyllodinea*), Silverleaf Nightshade (*Solanum elaeagnifolium*), Silversage (*Artemesia ludoviciana*), Silversheath Knotweed (*Polygonum argyrocoleon*), Skeletonweed (*Lygodesmia juncea*), Slender Aster (*Aster gracilis*), smallflower buttercup, Smallhead Sneezeweed (*Helenium microcephalum*), Smallseed Falseflax (*Camelina microcarpa*), smartweed, Smartweed, Pale (*Polygonum lapathifolium*), Smartweed, Pennsylvania (*Polygonum pensylvanicum*), Smooth Groundcherry (*Physalis subglabrata*), Smooth Sumac (*Rhus glabra*), snow speedweed, Snow-on-the-mountain (*Euphorbia marginata*), Southern *Sida* (*Sida acuta*), Spiny Pigweed (*Amaranthus spinosus*), Spiny Sowthistle (*Sonchus asper*), Sprawling Horseweed (*Calyptocarpus vialis*), Spreading Dayflower (*Commelina diffusa*), Spurge, Leafy (*Euphorbia esula*), Spurge, Prostrate (*Euphorbia humistrata*), Spurge, Toothed (*Euphorbia dentata*), Spurred Anoda (*Anoda cristata*), sticky chickweed, stinking mayweed/dogfennel, Sweet-potato (*Ipomea batatas*), swinecress, Tahoka Daisy (*Machaeranthera tanacetifolia*), tansymustard, tarweed fiddleneck, Texas Blueweed (*Helianthus ciliaris*), Texas Bullnettle (*Cnidoscolus texanus*), Thistle, Blessed Milk (*Silybum marianum*), Thistle, Distaff (*Carthamus lanatus*), Thistle, Malta Star (*Centaurea melitensis*), Thistle, Musk (noxious) (*Carduus nutans*), Thistle, Scotch (noxious) (*Onopordum acanthium*), Thistle, Tall (*Cirsium altissimum*), Thistle, Texas Purple (*Cirsium texanum*), Threadleaf Groundsel (*Senecio longilobus*), Toothcup (*Ammannia latifolia*), Trumpetcreeper (*Campsis radicans*), tumble, Twinleaf Sennia (*Senna roemeriana*), Velvetleaf (*Abutilon theophrasti*), Venice Mallow (*Hibiscus trionum*), Vetch (*Vicia* spp.), Virginia Copperleaf (*Acalypha virginica*), Virginia Creeper (*Parthenocissus quinquefolia*), Virginia Pepperweed (*Lepidium virginicum*), volunteer adzuki bean (*Vigna angularis*), volunteer lentils, volunteer peas, volunteer sunflower, Wandering Cudweed (*Gnaphalium pensylvanicum*), Waterhemlock (*Cicuta maculata*), Waterhemp (*Amaranthus tuberculatus*), Waterleaf (*Nama hispidum*), waterpod, Western Ragweed (*Ambrosia psilostachya*), Western Salsify (*Tragopogon dubuis*), White Foxglove Beardtongue (*Penstemon digitalis*), White Heath Aster (*Aster pilosus*), White Snakeroot (*Eupatorium rugosum*), Wild Buckwheat (*Polygonum convolvulus*), Wild Carrot (*Daucus carota*), wild chamomile, wild garlic, Wild Geranium (*Geranium carolinanum*), Wild Lettuce (*Lactuca serriola*), wild mustard (*Sinapis arvensis*), wild radish, Woollyleaf Bursage (*Ambrosia grayi*), Woollywhite, Chalkhill (*Hymenopappus tenuifolius*), Woollywhite, Yellow (*Hymenopappus flavescens*), Wright Eryngo (*Eryngium heterophyllum*), Yellow Rocket (*Barbarea vulgaris*), Yellow Sweetclover (*Melilotus indica*), Nightshade, Eastern black (*Solanum ptycanthum*), Cockspur (*Echinochola crusgalli*), Large crabgrass (*Digitaria sanginalis*), (*Septaria viridis*), Wild foxtail millet (*Setaria viridis*), *Acalypha australis*.

Preferably, such weeds include *Acalypha* spp., *Amaranthus* spp., *Brassica* spp., *Chenopodium* spp., *Daucus* spp., *Digitaria* spp., *Echinochola* spp., *Kochia* spp., *Polygonum* spp., *Rumex* spp., *Setaria* spp., *Solanum* spp., *Stellaria* spp., *Taraxacum* spp., *Xanthium* spp.

More preferably, such weeds include *Acalypha australis; Amaranthus retroflexus; Brassica kaber; Chenopodium album; Daucus carota; Digitaria sanginalis; Echinochola crusgalli; Kochia scoparia; Polygonum convolvulus; Rumex crispus; Setaria viridis; Solanum ptycanthum; Solanum sarrachoides; Stellaria media; Taraxacum officinale; Xanthium strumarium*.

The total amount of (A) and (B) is from 5% to 99% by weight of the composition.

The crystalline modification I of mesotrione may be present in the synergistic herbicidal composition of an embodiment of the invention in any suitable amount, and is generally present in an amount of from about 1% to about 90% by weight of the composition, preferably from about 1% to 80% by weight, more preferably from about 1% to about 70% by weight of the composition.

The crystalline modification I of tribenuron-methyl may be present in the synergistic herbicidal composition in any suitable amount, and is generally present in an amount of from about 1% to about 90% by weight of the composition, preferably from about 1% to about 80% by weight, more preferably from about 1% to about 70% by weight of the composition.

(A) and (B) may be employed in the composition, method or use of the invention in any suitable weight ratio. The weight ratio of the crystalline modification I of mesotrione and the crystalline modification I of tribenuron-methyl in the composition may be in the range of from about 99:1 to about 1:99, preferably from about 90:1 to about 1:90, more preferably from about 80:1 to about 1:80, still more preferably from about 70:1 to about 1:70, more preferably still from about 50:1 to about 1:50, 40:1 to about 1:40, about 40:1 to about 1:3.

In general, the application rate of the active ingredients depends on such factors as the type of weed, type of crop plant, soil type, season, climate, soil ecology and various other factors. The application rate of the composition for a given set of conditions can readily be determined by routine trials.

In general the composition or the method of an embodiment of the invention can be applied at an application rate of from about 0.005 kilograms/hectare (kg/ha) to about 5.0 kg/ha of the total amount of active ingredient (A) and (B) being applied. Preferably, the application rate is from about 0.01 kg/ha to about 3.0 kg/ha of the active ingredients.

Preferably, the application rate of the active ingredients is from 1 to 1000 g/ha of (A) the crystalline modification I of mesotrione and from 0.1 to 250 g/ha of (B) the crystalline modification I of tribenuron-methyl. More preferably, the application rate of the active ingredients is from 1 to 500 g/ha of (A) the crystalline modification I of mesotrione and from 0.1 to 100 g/ha of (B) the crystalline modification I of tribenuron-methyl.

As noted above, in an embodiment of the invention, (A) the crystalline modification I of mesotrione and (B) the crystalline modification I of tribenuron-methyl may be applied either separately or combined as part of a two-part herbicidal system, such as the composition of an embodiment of the invention. The composition is applied pre-planting, pre-emergence and/or post-emergence. The compositions of an embodiment of this invention can be formulated in conventional manner, for example by mixing (A) the crystalline modification I of mesotrione and (B) the crystalline modification I of tribenuron-methyl with appropriate auxiliaries. Suitable auxiliaries will depend upon such factors as the type of formulation and will be known to the person skilled in the art.

In particular, the composition may further comprise one or more auxiliaries selected from extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents. Such auxiliaries are known in the art and are commercially available. Their use in the formulation of the compositions of the present invention will be apparent to the person skilled in the art.

Suitable formulations for applying a combination of (A) and (B) include water-soluble concentrates (SL), emulsifiable concentrates (EC), emulsions, oil in water (EW), microemulsions (ME), suspension concentrates (SC), oil-based suspension concentrates (OD), flowable suspensions (FS), water-dispersible granules (WG), water-soluble granules (SG), wettable powders (WP), water soluble powders (SP), granules (GR), encapsulated granules (CG), fine granules (FG), macrogranules (GG), aqueous suspo-emulsions (SE), capsule suspensions (CS) and microgranules (MG). Preferred formulations include suspension concentrates (SC), water-dispersible granules (WG) and wettable powders (WP).

The composition may comprise one or more inert fillers. Such inert fillers are known in the art and available commercially. Suitable fillers include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates, and mixtures thereof. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks, and mixtures thereof.

The composition may optionally include one or more surfactants which are preferably non-ionic, cationic and/or anionic in nature and surfactant mixtures which have good emulsifying, dispersing and wetting properties, depending upon the active compound/compounds being formulated. Suitable surfactants are known in the art and are commercially available.

Suitable anionic surfactants can be both so-called water-soluble soaps and water-soluble synthetic surface-active compounds. Soaps which may be used include the alkali metal, alkaline earth metal or substituted or unsubstituted ammonium salts of higher fatty acid ($C_{10}$ to $C_{22}$), for example the sodium or potassium salt of oleic or stearic acid, or of natural fatty acid mixtures.

The surfactant may comprise an emulsifier, dispersant or wetting agent of ionic or nonionic type. Examples of such agents include salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, and phosphoric esters of polyethoxylated phenols or alcohols.

The presence of at least one surfactant is generally required when the active compound and/or the inert carrier and/or auxiliary/adjuvant are insoluble in water and the vehicle for the final application of the composition is water.

The composition may optionally further comprise one or more polymeric stabilizers. Suitable polymeric stabilizers that may be used in the present invention include, but are not limited to, polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are generally believed to impart stability to the composition, in turn allowing the composition to be formulated, stored, transported and applied.

Suitable anti-foaming agents for use in the compositions include all substances which can normally be used for this purpose in agrochemical compositions. Suitable anti-foaming agents are known in the art and are available commercially. Particularly preferred antifoam agents are mixtures of polydimethylsiloxanes and perfluroalkylphosphonic acids, such as the silicone anti-foaming agents available from GE or Compton.

Suitable solvents for use in the compositions may be selected from all customary organic solvents which thoroughly dissolve the active compounds employed. Again, suitable organic solvents for (A) and (B) are known in the art. The following may be mentioned as being preferred: N-methyl pyrrolidone, N-octyl pyrrolidone, cyclohexyl-1-pyrrolidone; and a mixture of paraffinic, isoparaffinic, cycloparaffinic and aromatic hydrocarbons (available commercially as SOLVESSO™200). Suitable solvents are commercially available.

Suitable preservatives include all substances which can normally be used for this purpose in agrochemical compositions of this type and again are well known in the art. Suitable examples that may be mentioned include PREVENTOL® (from Bayer AG) and PROXEL® (from Bayer AG).

The compositions may comprise an antioxidant. Suitable antioxidants are all substances which can normally be used for this purpose in agrochemical compositions, as is known in the art. Preference is given to butylated hydroxytoluene.

Suitable thickening agents for use in the compositions include all substances which can normally be used for this purpose in agrochemical compositions. Examples include xanthan gum, PVOH, cellulose and its derivatives, clay hydrated silicates, magnesium aluminum silicates or a mixture thereof. Again, such thickening agents are known in the art and available commercially.

The compositions may further comprise one or more solid adherents. Such adherents are known in the art and available commercially. They include organic adhesives, including tackifiers, such as celluloses of substituted celluloses, natural and synthetic polymers in the form of powders, granules, or lattices, and inorganic adhesives such as gypsum, silica, or cement.

In addition, depending upon the formulation, the composition according to an embodiment of the invention may also comprise water.

The formulated composition may for example be applied in spray form, for example employing appropriate dilutions using a diluent, such as water.

In the method and use of an embodiment of the invention, the combination of the active ingredients can be applied to the locus where control is desired, such as to the leaves of plants and/or the surrounding soil, by a convenient method. The "locus" refers to the place where the plants are growing, the place where the plant propagation materials of the plants are sown or the place where the plant propagation materials of the plants will be sown.

In the event, (A) and (B) are applied simultaneously in an embodiment of the invention, they may be applied as a composition containing (A) and (B), in which case (A) and (B) can be obtained from a separate formulation source and mixed together (known as a tank-mix, ready-to-apply, spray broth, or slurry), optionally with other pesticides, or (A) and (B) can be obtained as a single formulation mixture source (known as a pre-mix, concentrate, formulated compound (or product)), and optionally mixed together with other pesticides.

In a preferred embodiment, the method and use employ a composition according to an embodiment of the invention.

The compositions according to an embodiment of the invention are distinguished by the fact that they are especially well tolerated by crop plants being treated and are environmentally friendly.

Although the invention is described with reference to preferred embodiments and examples thereof, the scope of the invention is not limited only to these described embodiments. As will be apparent to persons skilled in the art, modifications and adaptations to the above-described invention can be made without departing from the spirit and scope of the invention, which is defined by the appended claims.

Embodiments of the invention will now be described, for illustrative purposes only, by way of the following examples.

EXAMPLES

Example 1—Preparation of the Crystalline Modification I Mesotrione

The crystalline I modification of mesotrione was prepared according to the method as mentioned in WO 2006021743.

Mesotrione enolate suspension was filtered to remove any excess solid enolate. 50 mL of the filtered solution was placed in a reaction flask and heated to 40° C. pH of the solution was adjusted to 2.8 by adding 10% HCl over 20 minutes. Crystals were allowed to stir for 20 minutes before isolation by filtration. The crystals were then washed with water and sucked dry on the filter.

Example 2—Preparation of the Crystalline Modification II Mesotrione

The crystalline II modification of mesotrione was prepared according to the method as mentioned in WO 2006021743.

Mesotrione crystals were stirred with water in a reaction flask. pH was increased to 12 by adding NaOH. 1.5 mL of 10% HCl was added over 15 minutes to reduce the pH of the solution to pH 4. Crystals were obtained.

Example 3—Preparation of amorphous tribenuron-methyl

Tribenuron-methyl in an amorphous form was prepared according to a method mentioned in EP 0202830.

To a solution of 2-carbomethoxybenzenesul-fonyl isocyanate (22.4 g 93.0 mmol) in dichloromethane (100 mL) was added 2-methoxy-4-methyl-6-methylamino-1,3,5-triazine (10.7 g, 69.6 mmol), followed by a catalytic amount of 1,4-diaza[2.2.2]bicyclooctane. After stirring overnight at ambient temperature under a nitrogen atmosphere, the reaction mixture was concentrated in vacuo. The residue was triturated with diethyl ether and then washed with 1-chlorobutane to yield the title compound as a white powder (28.8 g).

As shown in FIG. 1, there is no significant individual signal or peak in the X-ray powder diffraction pattern. The result indicates the product prepared in accordance with the disclosure of EP 0202830 A1 is amorphous.

Example 4—Preparation of the crystalline modification I tribenuron-methyl

Tribenuron-methyl (10 g) sample prepared in Example 3 was added to a 3 necked round bottom flask having methanol (60 mL). The resulting slurry was heated to 50° C. to get a homogeneous solution. The solution was filtered to remove any insoluble material. The solution was slowly cooled to room temperature. Product was precipitated as fine crystal during cooling and the mixture was stirred at room temperature for 2 hours. Then, the slurry was filtered, washed with methanol (3 mL). The filtered crystals were dried under vacuum to remove methanol from the crystal. The crystal obtained has a purity of >98% and the recovered yield was found to be not less than 80%. The obtained crystal was analyzed by DSC, IR and X-ray powder diffraction.

Figure 2:
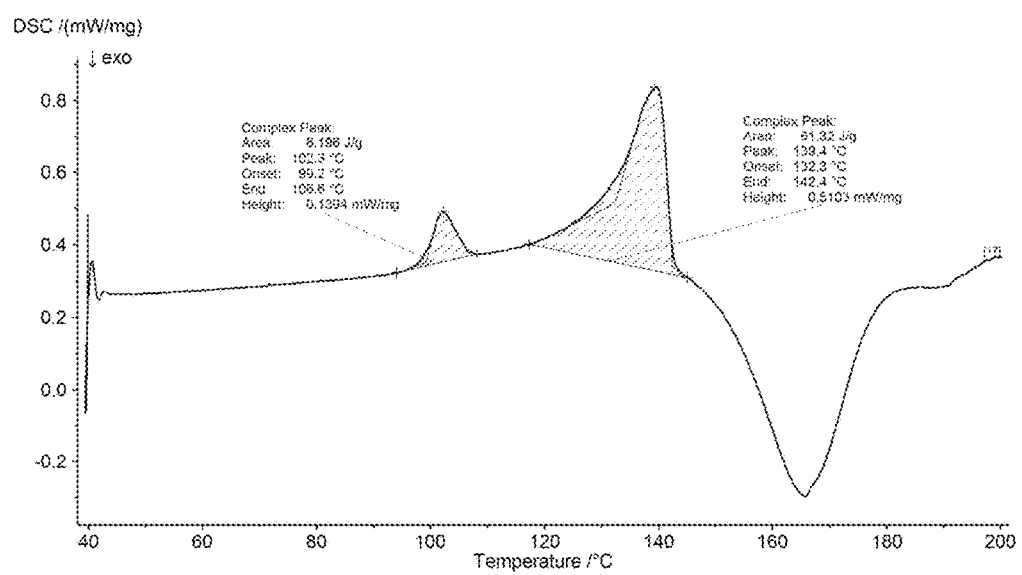
FIG. 2 is a graph showing the results of a Differential Scanning calorimetry (DSC) scan of an embodiment of crystalline modification I of tribenuron-methyl.

Differential scanning calorimetry (DSC) shows an endothermic melting peak with onset at 132.3° C. and peak maximum at 139.4° C. as shown in FIG. 2.

Figure 3:
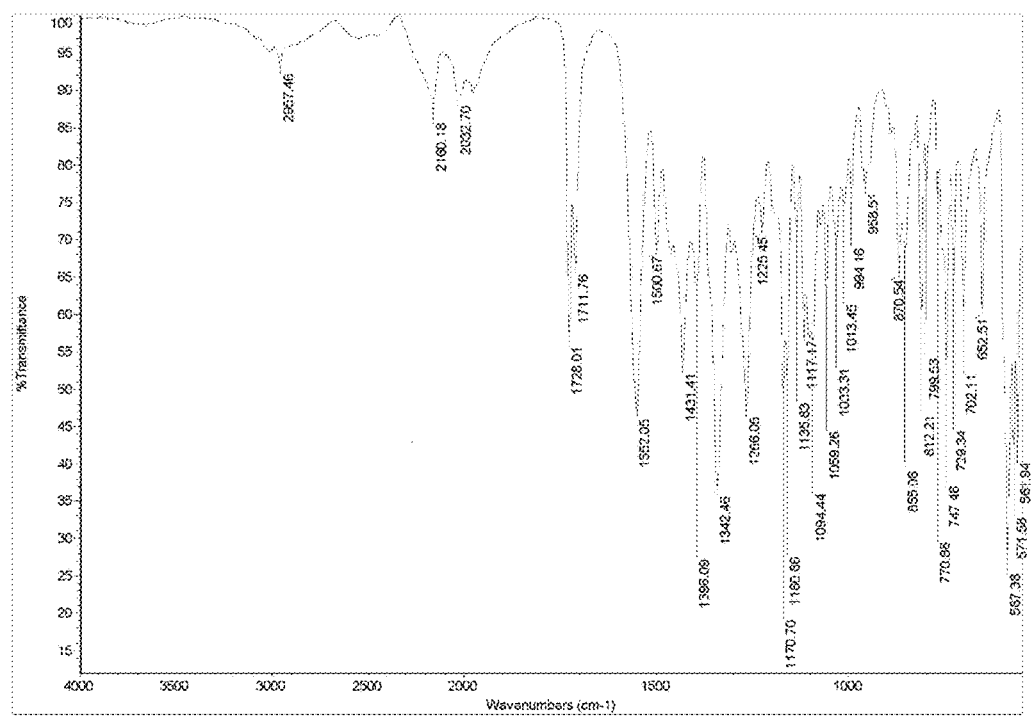
FIG. 3 is a graph showing the results of an infrared (IR) spectrum of an embodiment of crystalline modification I of tribenuron-methyl.

IR spectrum of the crystalline modification I of tribenuron-methyl shows the functional group characteristic vibrations at 2957.46, 2160.18, 2032.70, 1728.01 and 1552.05 $cm^{-1}$ as shown in FIG. 3.

Figure 4:
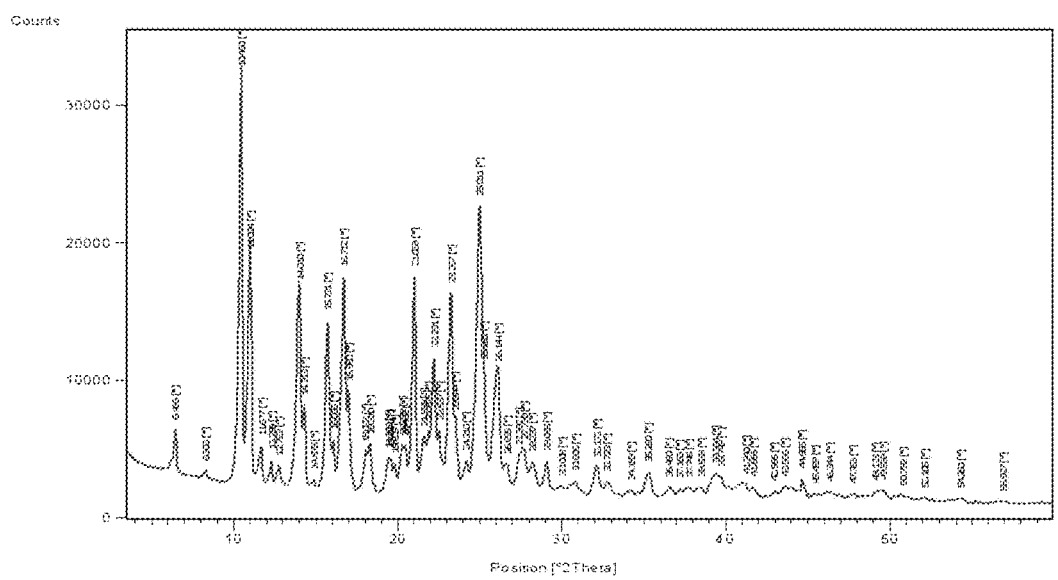
FIG. 4 is a graph showing the results of an X-ray powder diffractogram of an embodiment of crystalline modification I of tribenuron-methyl.

The crystalline modification I of tribenuron-methyl has the X-ray powder diffractogram shown in FIG. 4 with reflexes summarized in Table B below. The X-ray powder diffractogram was taken using a diffractometer from in reflection geometry in the range from 3°-60° with increments of 0.03° using Cu-Kα radiation at 25° C.

TABLE B

X-ray powder diffractogram reflexes of crystalline modification I of tribenuron-methyl Crystal Form A

| 2 θ (°) | d (Å) |
|---|---|
| 6.47 ± 0.2 | 13.67 ± 0.05 |
| 10.46 ± 0.2 | 8.46 ± 0.05 |
| 11.02 ± 0.2 | 8.03 ± 0.05 |
| 14.01 ± 0.2 | 6.32 ± 0.05 |
| 15.73 ± 0.2 | 5.63 ± 0.05 |
| 16.71 ± 0.2 | 5.31 ± 0.05 |
| 16.98 ± 0.2 | 5.22 ± 0.05 |
| 21.04 ± 0.2 | 4.22 ± 0.05 |
| 22.23 ± 0.2 | 4.00 ± 0.05 |
| 23.26 ± 0.2 | 3.82 ± 0.05 |
| 25.01 ± 0.2 | 3.56 ± 0.05 |
| 26.14 ± 0.2 | 3.41 ± 0.05 |

Formulation Examples

Water-dispersible granule (WG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), Potassium carbonate (balance to 100%)) under compressed air, then wetting, extruding and drying to obtain water-dispersible granule.

For example,

The crystalline modification I of mesotrione 50%
The crystalline modification I of tribenuron-methyl 5%
SUPRALATE® (sodium lauryl sulfate, Witco Inc., Greenwich) 0.5%
REAX® 88B (sodium lignosulfonate, Westvaco Corp) 5%
Potassium carbonate Balance to 100%

Aqueous suspension concentrates (SC) were prepared by mixing finely ground active ingredients with auxiliaries (10% Propylene glycol, 5% Tristyrylphenol ethoxylates, 1% Sodium lignosulfonate, 1% Carboxymethylcellulose, 1% Silicone oil (in the form of a 75% emulsion in water), 0.1% Xanthan gum, 0.1% NIPACIDE BIT 20, Water (Balance to 1 L).

For example,

The crystalline modification I of mesotrione 40%
The crystalline modification I of tribenuron-methyl 2%
Propylene glycol 10%
Tristyrylphenol ethoxylates 5%
Sodium lignosulfonate 1%
Carboxymethylcellulose 1%
Silicone oil (in the form of a 75% emulsion in water) 1%
Xanthan gum 0.1%
NIPACIDE BIT 20 0.1%
Water Balance to 100%

Water-soluble granules (SG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), 2% Sodium hydrogen carbonate (NaHCO3), Potassium sulfate (balance to 100%)) under compressed air, then wetting, extruding and drying to obtain water-soluble granules.

For example,

The crystalline modification I of mesotrione 20%
The crystalline modification I of tribenuron-methyl 8%
SUPRALATE® (sodium lauryl sulfate, Witco Inc., Greenwich) 0.5%
REAX® 88B (sodium lignosulfonate, Westvaco Corp) 5%
Sodium hydrogen carbonate ($NaHCO_3$) 2%
Potassium sulfate Balance to 100%

Formulations were prepared according to the methods above (Table A):

TABLE A

| | | Mesotrione (%) | | | Tribenuron-methyl (%) |
|---|---|---|---|---|---|
| No | Formulation type | I | II | Amorphous | I |
| 1 | SC | 40 | / | / | / |
| 2 | SC | / | 40 | / | / |
| 3 | WG | / | / | 50 | / |
| 4 | WG | / | / | / | 50 |
| 5 | SC | 40 | / | 2 | / |
| 6 | SC | / | 40 | 2 | / |
| 7 | SC | 40 | / | / | 2 |
| 8 | SC | / | 40 | / | 2 |
| 9 | SC | 40 | / | / | 2 |
| 10 | WG | 50 | / | / | 5 |
| 11 | SC | 40 | / | / | 1 |
| 12 | SG | 20 | / | / | 8 |
| 13 | WG | 65 | / | / | 2 |
| 14 | SC | 30 | / | / | 25 |
| 15 | SG | 10 | / | / | 30 |

Biological Examples 1

Barley, wheat, corn and oilseed rape plants were sown side by side in the field. Different types of weeds and their relative density were recorded and are listed in Table 1 below. Formulations of Examples 1 to 8 above were applied 50 days after planting. After spraying the plants, the beds were maintained for about 2 weeks. Two weeks after application, the beds were examined to determine the efficiency of the treatment by again recording the relative density. The results are set forth below in Table 2 below.

TABLE 1

| Type of weed | |
|---|---|
| Type of weed | Relative density (%) |
| Echinochola crusgalli | 20 |
| Chenopodium album | 25 |
| Kochia scoparia | 10 |
| Digitaria sanginalis | 5 |
| Brassica kaber | 5 |
| Daucus carota | 10 |
| Setaria viridis | 25 |

TABLE 2

Efficiency (%)

| Formulation Examples | Mesotrione (g/ha) | Tribenuron-methyl (g/ha) | Echinochola crusgalli | Chenopodium album | Kochia scoparia | Digitaria sanginalis | Brassica kaber | Daucus carota | Setaria viridis |
|---|---|---|---|---|---|---|---|---|---|
| Untreated | 0 | 0 | 0% | 0% | 0% | 0% | 0% | 0% | 0% |
| Example 1 | 100 | 0 | 25 | 40 | 35 | 35 | 35 | 30 | 30 |
| Example 2 | 100 | 0 | 30 | 40 | 30 | 30 | 35 | 30 | 25 |
| Example 3 | 0 | 20 | 20 | 30 | 30 | 25 | 35 | 35 | 25 |
| Example 4 | 0 | 20 | 25 | 40 | 35 | 25 | 35 | 30 | 30 |
| Example 5 | 100 | 5 | 70 | 75 | 65 | 70 | 70 | 75 | 65 |
| Example 6 | 100 | 5 | 60 | 65 | 60 | 55 | 60 | 65 | 55 |
| Example 7 | 100 | 5 | 100 | 100 | 100 | 100 | 95 | 100 | 95 |
| Example 8 | 100 | 5 | 70 | 70 | 65 | 70 | 65 | 75 | 70 |

Biological Examples 2

Corn, oat, sugarcane and rye plants were sown side by side in the field. Different types of weeds and their relative density were recorded and are listed in Table 3 below. Formulations of Examples 9 to 15 above were applied 50 days after planting. After spraying the plants, the beds were maintained for about 2 weeks. Two weeks after application, the beds were examined to determine the efficiency of the treatment by gain recording the relative density. The results are set forth below in Table 4 below.

TABLE 3

| Type of weed | |
|---|---|
| Type of weed | Relative density (%) |
| Stellaria media | 15 |
| Xanthium strumarium | 20 |
| Rumex crispus | 5 |
| Taraxacum officinale | 10 |
| Solanum sarrachoides | 10 |
| Solanum ptycanthum | 20 |
| Amaranthus retroflexus | 5 |

TABLE 3-continued

| Type of weed | |
|---|---|
| Type of weed | Relative density (%) |
| Polygonum convolvulus | 5 |
| Acalypha australis | 10 |

TABLE 4

Efficiency (%)

| Formulation Examples | Mesotrione (g/ha) | Tribenuron-methyl (g/ha) | Stellaria media | Xanthium strumarium | Rumex crispus | Taraxacum officinale | Solanum sarrachoides | Solanum ptycanthum | Amaranthus retroflexus | Polygonum convolvulus | Acalypha australis |
|---|---|---|---|---|---|---|---|---|---|---|---|
| Untreated | 0 | 0 | 0 | 0 | 0 | 0 | 0 | 0 | 0 | 0 | 0 |
| Example 9 | 100 | 5 | 95 | 100 | 100 | 100 | 95 | 100 | 95 | 100 | 95 |
| Example 10 | 125 | 12.5 | 100 | 95 | 100 | 100 | 95 | 100 | 95 | 100 | 95 |
| Example 11 | 200 | 5 | 100 | 95 | 100 | 100 | 95 | 100 | 95 | 100 | 95 |
| Example 12 | 50 | 20 | 95 | 95 | 100 | 100 | 95 | 100 | 95 | 100 | 100 |
| Example 13 | 325 | 10 | 100 | 100 | 100 | 100 | 95 | 95 | 95 | 100 | 95 |
| Example 14 | 37.5 | 31.25 | 100 | 100 | 100 | 95 | 95 | 100 | 95 | 100 | 95 |
| Example 15 | 20 | 60 | 100 | 100 | 100 | 100 | 95 | 95 | 100 | 95 | 100 |

The invention claimed is:
1. A composition comprising a herbicidally effective synergistic amount of
   (A) the crystalline modification I of 2-(4-mesyl-2-nitrobenzoyl)cyclohexane-1,3-dione (mesotrione); and
   (B) the crystalline modification I of methyl 2-[[[[(4-methoxy-6-methyl-1,3,5-triazin-2-yl)methylamino]

carbonyl]amino]sulfonyl]benzoate (tribenuron-methyl), wherein the crystalline modification I of tribenuron-methyl is crystallized using methanol and/or ethanol, and the crystalline modification I of tribenuron-methyl exhibits each of the following reflexes as 2θ values in X-ray powder diffractogram recorded using Cu—Kα radiation at 25° C.:

| | |
|---|---|
| 2θ = 6.47 ± 0.2 | (1) |
| 2θ = 10.46 ± 0.2 | (2) |
| 2θ = 11.02 ± 0.2 | (3) |
| 2θ = 14.01 ± 0.2 | (4) |
| 2θ = 15.73 ± 0.2 | (5) |
| 2θ = 16.71 ± 0.2 | (6) |
| 2θ = 16.98 ± 0.2 | (7) |
| 2θ = 21.04 ± 0.2 | (8) |
| 2θ = 22.23 ± 0.2 | (9) |
| 2θ = 23.26 ± 0.2 | (10) |
| 2θ = 25.01 ± 0.2 | (11) |
| 2θ = 26.14 ± 0.2 | (12). |

2. The composition according to claim 1, wherein the weight ratio of (A) to (B) is in the range of from about 99:1 to about 1:99.

3. The composition according to claim 2, wherein the weight ratio of (A) to (B) is in the range of from about 50:1 to about 1:50.

4. The composition according to claim 3, wherein the weight ratio of (A) to (B) is in the range of from about 40:1 to about 1:3.

5. The composition according to claim 1, wherein the total amount of (A) and (B) is from 5% to 99% by weight of the composition.

6. The composition according to claim 5, wherein the composition comprises, by weight, from about 1% to about 90% of (A) and from about 1% to about 90% of (B).

7. The composition according to claim 5, wherein the composition comprises, by weight, from about 1% to about 70% of (A) and from about 1% to about 70% of (B).

8. The composition according to claim 1, further comprising one or more auxiliaries selected from the group consisting of extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents.

9. The composition according to claim 1, formulated as a water-soluble concentrate (SL), an emulstifiable concentrate (EC), an emulsion, oil in water (EW), a micro-emulsion (ME), a suspension concentrate (SC), an oil-based suspension concentrate (OD), a flowable suspension (FS), a water-dispersible granule (WG), a water-soluble granule (SG), a wettable powder (WP), a water soluble powder (SP), a granule (GR), an encapsulated granule (CG), a fine granule (FG), a macrogranule (GG), an aqueous suspo-emulsion (SE), a capsule suspension (CS) or a microgranule (MG).

10. A method of controlling undesirable plant growth comprising applying to the plant or to the locus thereof a herbicidally effective amount of the herbicidal composition of claim 1.

11. The method according to claim 10, wherein the plant growth is being controlled in a crop comprising cereals, sugarcane, vegetables and oil plants.

12. The method according to claim 10, wherein the plant growth being controlled is of one or more of broadleaf weeds and grasses.

13. The method according to claim 12, wherein the plant growth being controlled is one or more of *Acalypha* spp., *Amaranthus* spp., *Brassica* spp., *Chenopodium* spp., *Daucus* spp., *Digitaria* spp., *Echinochola* spp., *Kochia* spp., *Polygonum* spp., *Rumex* spp., *Setaria* spp., *Solanum* spp., *Stellaria* spp., *Taraxacum* spp., or *Xanthium* spp.

14. The method according to claim 10, wherein the composition is applied at an application rate of about 0.005 kilograms/hectare (kg/ha) to about 5.0 kg/ha of the total amount of active ingredient (A) and (B) being applied.

15. The method according to claim 14, wherein the composition is applied at an application rate of from about 0.01 kg/ha to about 3.0 kg/ha of the total amount of active ingredient (A) and (B) being applied.

16. The method according to claim 15, wherein the composition is applied at an application rate of from 1 to 1000 g/ha of (A) and from 0.1 to 250 g/ha of (B).

17. The method according to claim 16, wherein the composition is applied at an application rate of from 1 to 500 g/ha of (A) and 0.1 to 100 g/ha of (B).

18. The method according to claim 10, wherein the composition is applied pre-planting, pre-emergence and/or post-emergence.

19. A method of controlling undesirable plant growth at a locus comprising applying to the locus herbicidally effective amounts of (A) the crystalline modification I of 2-(4-mesyl-2-nitrobenzoyl)cyclohexane-1,3-dione (mesotrione) and (B) the crystalline modification I of 2-[[[[(4-methoxy-6-methyl-1,3,5-triazin-2-yl)methylamino]carbonyl]amino]sulfonyl]benzoate (tribenuron-methyl), wherein the crystalline modification I of tribenuron-methyl is crystallized using methanol and/or ethanol, and the crystalline modification I of tribenuron-methyl exhibits each of the following reflexes as 2θ values in X-ray powder diffractogram recorded using Cu—Kα radiation at 25° C.:

| | |
|---|---|
| 2θ = 6.47 ± 0.2 | (1) |
| 2θ = 10.46 ± 0.2 | (2) |
| 2θ = 11.02 ± 0.2 | (3) |
| 2θ = 14.01 ± 0.2 | (4) |
| 2θ = 15.73 ± 0.2 | (5) |
| 2θ = 16.71 ± 0.2 | (6) |
| 2θ = 16.98 ± 0.2 | (7) |
| 2θ = 21.04 ± 0.2 | (8) |
| 2θ = 22.23 ± 0.2 | (9) |
| 2θ = 23.26 ± 0.2 | (10) |
| 2θ = 25.01 ± 0.2 | (11) |
| 2θ = 26.14 ± 0.2 | (12). |

20. The method according to claim 19, wherein the plant growth is being controlled in a crop comprising cereals, sugarcane, vegetables and oil plants.

21. The method according to claim 19, wherein (A) and (B) are applied to the locus at the same time.

22. The method according to claim 19, wherein (A) and (B) are applied to the locus consecutively.

23. The method according to claim 19, wherein the plant growth being controlled is of one or more of broadleaf weeds and grasses.

24. The method according to claim 23, wherein the plant growth being controlled is one or more of *Acalypha* spp., *Amaranthus* spp., *Brassica* spp., *Chenopodium* spp., *Daucus* spp., *Digitaria* spp., *Echinochola* spp., *Kochia* spp., *Polygonum* spp., *Rumex* spp., *Setaria* spp., *Solanum* spp., *Stellaria* spp., *Taraxacum* spp., or *Xanthium* spp.

25. The method according to claim 19, wherein the weight ratio of (A) to (B) applied is in the range of from about 99:1 to about 1:99.

26. The method according to claim 25, wherein the weight ratio of (A) to (B) applied is in the range of from about 80:1 to about 1:80.

27. The method according to claim 26, wherein the weight ratio of (A) to (B) applied is in the range of from about 40:1 to about 1:3.

28. The method according to claim 19, wherein (A) and (B) are applied at an application rate of about 0.005 kilograms/hectare (kg/ha) to about 5.0 kg/ha of the total amount of active ingredient (A) and (B) being applied.

29. The method according to claim 28, wherein (A) and (B) are applied at an application rate of from about 0.01 kg/ha to about 3.0 kg/ha of the total amount of active ingredient (A) and (B) being applied.

30. The method according to claim 29, wherein (A) and (B) are applied at an application rate of from 1 to 1000 g/ha of (A) and from 0.1 to 250 g/ha of (B).

31. The method according to claim 30, wherein (A) and (B) are applied at an application rate of from 1 to 500 g/ha of (A) and 0.1 to 100 g/ha of (B).

32. The method according to claim 19, wherein (A) and (B) are applied pre-planting, pre-emergence and/or post-emergence.

\* \* \* \* \*